United States Patent [19]

Stütz

[11] Patent Number: 4,737,516

[45] Date of Patent: Apr. 12, 1988

[54] BENZOTHIENYLALLYLAMINES PROCESSES FOR THEIR PRODUCTION AND THEIR USE AS PHARMACEUTICALS

[75] Inventor: Anton Stütz, Maria Enzersdorf, Austria

[73] Assignee: Sandoz Ltd., Basel, Switzerland

[21] Appl. No.: 858,417

[22] Filed: May 1, 1986

Related U.S. Application Data

[63] Continuation of Ser. No. 755,665, Jul. 16, 1985, abandoned, which is a continuation of Ser. No. 664,694, Oct. 25, 1984, abandoned, which is a continuation of Ser. No. 463,460, Feb. 3, 1983, abandoned.

[30] Foreign Application Priority Data

Feb. 3, 1982 [CH] Switzerland ............................ 656/82

[51] Int. Cl.$^4$ .................... A01N 43/02; C07D 333/52
[52] U.S. Cl. ........................................ 514/443; 549/49
[58] Field of Search ........................... 549/49; 514/443

[56] References Cited

U.S. PATENT DOCUMENTS 4,680,291 7/1987 Hamberger et al. .................. 549/49

FOREIGN PATENT DOCUMENTS 0000896 3/1979 European Pat. Off. .
0024587 11/1981 European Pat. Off. .

Primary Examiner—Alan Siegel
Attorney, Agent, or Firm—Gerald D. Sharkin; Robert S. Honor; Thomas O. McGovern

[57] ABSTRACT

Benzothienyldialkylallylamines wherein the amine side chain is attached to the ring via an alkyl radical and is either in 4-, 5-, 6- or 7-position or if not bears tertiary alkylethynyl or alkenylethynyl as its terminal group, which are useful, in particular, as anti-mycotic agents.

22 Claims, No Drawings

BENZOTHIENYLALLYLAMINES PROCESSES FOR THEIR PRODUCTION AND THEIR USE AS PHARMACEUTICALS

This is a continuation of application Ser. No. 755,665, filed July 16, 1985, now abandoned, which in turn is a continuation of application Ser. No. 664,694, filed Oct. 25, 1984, now abandoned, which in turn is a continuation of application Ser. No. 463,460, filed Feb. 3, 1983, now abandoned.

The invention concerns benzothienylallylamines processes for their production and their use as pharmaceuticals.

In one aspect the invention comprises benzothienyl-dialkylallylamine, wherein the amine side chain is attached to the ring via an alkyl radical and is either in 4-, 5-, 6- or 7-position or if not bears tertiary alkylethynyl or alkenylethynyl as its terminal group.

More particularly the invention concerns compounds of formula I

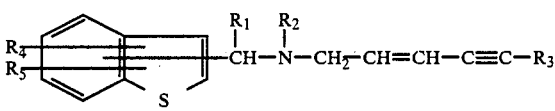

wherein
$R_1$ represents hydrogen or methyl,
$R_2$ represents methyl or ethyl,
$R_3$ represents tertiary alkyl or an alkenyl group; and
$R_4$ and $R_5$ represent, independently of each other, hydrogen, halogen, hydroxy, lower alkynyl, cyano, formyl, lower-alkoxy, lower alkoxycarbonyl, lower alkylcarbonyl, lower alkyl which is unsubstituted or bears one or more substituents selected from halogen, cyano, hydroxy, lower alkylthio and lower alkoxy; or lower alkenyl which is unsubstituted or bears one or more substituents selected from halogen and cyano, in free base form or in the form of an acid addition salt.

EP Publication No. 0,024,587 discloses a wide range of aromatic allylamines without specifically disclosing compounds of the type comprising the present invention. It has now been found that in tests such as hereinafter described the compounds of the present invention not only exhibit high activity against dermatophytes but also a surprisingly high activity against candida spp. not possessed to the same degree by the compounds of EP No. 0024587.

The compounds of the invention can be prepared e.g. by
(a) reacting a compound of formula II

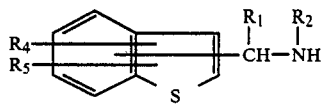

with a compound of formula III

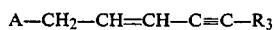

or
(b) reacting a compound of formula IV

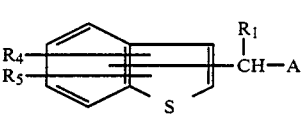

with a compound of formula V

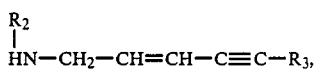

whereby in the formulae II, III, IV and V
$R_1$, $R_2$, $R_3$, $R_4$ and $R_5$ are as defined under formula I and
A represents a leaving group,
and recovering the compound thus obtained in free base form or in the form of an acid addition salt. The remaining benzothienyldialkylallylamines of the invention can be prepared analogously.

Processes (a) and (b) can be carried out in conventional manner, for example in a solvent, inert under the reaction conditions, such as a lower alcohol, e.g. ethanol, optionally in mixture with water; an aromatic hydrocarbon such as benzene or toluene; a cyclic ether, such as dioxane; or a carboxylic acid dialkylamide such as dimethylformamide and at reaction temperatures of between room temperature (which is preferred) and the boiling point of the reaction mixture. Leaving group A can for example be halogen e.g. chlorine or bromine or an organic sulphonyloxy group having 1 to 10 carbon atoms, e.g. alkarylsulphonyloxy such as tosyloxy or alkylsulphonyloxy such as mesyloxy. The reaction is conveniently carried out, when appropriate, in the presence of an acid binding agent, e.g. an alkali or alkaline earth metal hydroxide or carbonate such as sodium potassium carbonate.

The compounds of formula I may be converted in conventional manner into their acid addition salts and vice versa.

The compounds of the formula I and their intermediates can be obtained in the form of isomeric mixtures of the various cis/trans isomers which can be separated according to established methods.

Any lower alkyl radical present as or in a substituent can be straight or branch-chained and has preferably 1 to 4 carbon atoms, especially 1 or 2 carbon atoms; alkynyl or alkenyl groups can be straight or branch-chained and have preferably 2 to 6 carbon atoms especially 2 to 4 as ring substituents or 3 or 4 (alkenyl) as $R_3$, examples are vinyl and ethynyl as ring substituents and allyl (preferably β-allyl) as $R_3$. Tertiary alkyl groups as $R_3$ contain preferably 4 to 10 especially 4 to 6 carbon atoms e.g. t.-butyl. Halogen represents fluorine, chlorine or bromine preferably chlorine or bromine.

The starting materials of formula II are in part new and can be prepared in conventional manner e.g. by reacting a compound of formula VI

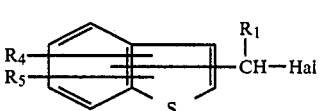

with a compound of formula VII $R_2$—$NH_2$    VII whereby $R_1$, $R_2$, $R_4$ and $R_5$ are as defined under formula I and Hal represents halogen.

This process can be performed analogously to processes (a) and (b) described above.

The starting materials of formulae III and V are in part new and can be prepared in conventional manner, e.g. according to the following scheme

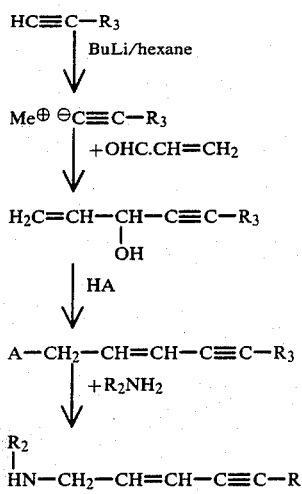

($R_1$, $R_2$, $R_3$ and A as defined above $Me^{\oplus}$=metalcation).

Reaction conditions are those conventionally employed in such reactions whereby the various intermediates can, where appropriate, be reacted further without isolation. Where isolation takes place it is carried out in conventional manner.

The remaining starting materials and intermediate compounds are either known or can be prepared according to known methods.

The compounds of formula I exhibit chemotherapeutic activity. In particular, they exhibit antimycotic activity, as indicated in vitro in various families and types of mycetes, including Trichophyton spp., Aspergillus spp., Microsporum spp., *Sporotrix schenkii* and especially Candida spp., at concentrations of, for example 0.1 to 25 ug/ml, and in vivo in the experimental skin mycosis model in guinea pigs. The test substance is administered daily for 7 days beginning 24 hours after the infection either on local application by rubbing the test substance (taken up in polyethylene glycol) on the skin surface, or perorally or sub-cutaneously, the test substance being administered as a suspension. The Candida activity is shown in vivo employing conventional intravaginal/intrauterine- or disseminated-infection models on mice or rats. The activity is shown on local application at concentrations of for example 0.01 to 0.5%. The oral activity is shown in vivo in the guinea-pig-trichophytosis at dosages of, for example, 2 to 70 mg/kg.

The compounds may therefore be used as antimycotic agents. For this use, the effective dosage will, of course, vary depending on the particular compound employed, the mode of administration and the treatment desired. However, in general, satisfactory results can be obtained when the compounds are administered at a daily dosage of from about 1 to 30 mg/kg of animal body weight, suitably given in divided doses two to four times daily. For most large mammals, the total daily dosage is from about 70 to 2000 mg and dosage forms suitable for internal administration comprise about 17.5 to 1000 mg of the compound in admixture with a solid or liquid chemotherapeutical carrier or diluent.

The compounds of formula I may be administered in similar manner to known standards for use in such indications e.g. Clotrimazol.

The suitable daily dosage for a particular compound will depend on a number of factors such as its relative potency of activity. It has, for example, been determined that the preferred compound of this invention namely (E)-N-(3-chloro-7-benzo[b]thienylmethyl)-N-methyl-6,6-dimethyl-hept-2-en-4-ynamine exhibited an MIC value in a series dilution test against Candida parapsilosis of 0.02 μg/ml compared with 0.2 for Clotrimazol. It is therefore indicated that these compounds may be administered at similar or lower dosages than conventionally employed for Clotrimazol.

The compounds may be used in free base form or in the form of chemotherapeutically acceptable acid addition salts. Such salt forms exhibit the same order of activity as the free base forms. Suitable such salt forms are e.g. hydrochloride, hydrogen fumarate or naphthaline-1,5-disulphonate.

The invention therefore also concerns a method of treating diseases or infections caused by mycetes which comprises administering to a subject in need of such treatment an effective amount of a compound of formula I or a chemotherapeutically acceptable acid addition salt thereof as well as compounds of formula I or chemotherapeutically acceptable acid addition salts thereof for use as chemotherapeutic agents especially as anti-mycotics.

The compounds may be admixed with conventional chemotherapeutically acceptable diluents and carriers, and, optionally, other excipients and administered e.g. orally in such forms as tablets or capsules. The compounds may alternatively be administered topically (in such conventional forms as ointments or creams), parenterally or intravenously. The concentrations of the active substance will, of course, vary depending on the compound employed, the treatment desired and the nature of the form etc. In general, however, satisfactory results are obtained e.g. in topical application forms at concentrations of from 0.05 to 5, in particular 0.1 to 1 wt.%.

Such compositions also form part of the invention.

Preferred meanings for the substituents are as follows:
$R_1$=hydrogen
$R_2$=methyl
$R_3$=
(a) $C_{4-10}$alkyl
(b) $C_{4-6}$alkyl
(c) t.butyl or t.-pentyl, especially t.butyl
(d) $C_{3-6}$alkenyl
(e) allyl, especially β-allyl
$R_4$, $R_5$=hydrogen, or
(a) $C_{1-4}$alkyl
(b) $C_{1-2}$alkyl, especially methyl
(c) halogen, especially chlorine
(d) $C_{1-4}$haloalkyl, especially $CF_3$
(e) $C_{2-5}$alkylcarbonyl, especially acetyl,
(f) $C_{1-4}$hydroxyalkyl, especially —$CH_2OH$
(g) cyano
(h) $C_{1-4}$alkylthio or -alkoxy e.g. methylthio or methoxy (i) formyl (j) $C_{2-4}$alkenyl (e.g. vinyl) optionally halogen substituted (k) $C_{2-4}$alkynyl e.g. ethynyl whereby one of $R_4$ and $R_5$ is preferably hydrogen.

The allylamine side chain is preferably attached to the benzene ring especially in the 4- or 7-position, whereby the latter is more preferred. Substituents present as $R_4$ and/or $R_5$ are preferably in the thienyl ring i.e. at position 2 and/or 3.

Compounds in which the double bond proximal to the nitrogen in the chain has the trans (E) configuration are preferred.

A particularly preferred single compound is: (E)-N-(3-chloro-7-benzo[b]thienylmethyl)-N-methyl-6,6-dimethyl-hept-2-en-4-ynamine.

The following examples illustrate the invention whereby temperatures are given in degrees centigrade.

EXAMPLE 1

N-(7-benzo[b]thienylmethyl)-N-methyl-6,6-dimethyl-hept-2-en-4-ynamine in (E)- and (Z)-form (compounds (1a) and (1b) respectively; process (a))

12 g of 1-bromo-6,6-dimethyl-hept-2-en-4-yne are added dropwise to a mixture of 10.5 g N-(7-benzo[b]-thienylmethyl)methylamine, 8.2 g of potassium carbonate and 100 ml of dimethylformamide and stirred overnight. The reaction mixture is filtered and the solvent removed under vacuum. The residue is partitioned between ether and saturated aq. $NaHCO_3$ and the organic phase dried, concentrated in a rotary evaporator and chromatographed over silica gel (eluant: toluene/ethylacetate=4/1). This yields first the (E)- and then the (Z)-isomer as oils. M.p. of the (E)-hydrochloride=148°–158°.

EXAMPLE 2

N-(3-chloro-7-benzo[b]thienylmethyl)-N-methyl-6,6-dimethyl-hept-2-en-4-ynamine in (E)- and (Z)-form (compounds (2a) and (2b) respectively; process (b)).

690 mg of N-(6,6-dimethyl-hept-2-en-4-ynyl)methylamine dissolved in dimethylformamide are added dropwise to 1.4 g of 7-bromomethyl-3-chloro-benzo[b]thiophene and 480 mg of $NaCO_3$ in 40 ml of dimethylformamide and stirred overnight. The reaction mixture is concentrated under vacuum and the residue taken up in ether/water. The organic phase is washed with saturated $NaHCO_3$, dried and concentrated by evaporation. The residue is chromatographed over silica gel (eluant: toluene/ethylacetate=95/5) to yield first the (E)- and then the (Z)-isomer as oils. M.p. of the (E)-hydrochloride=180°–184°.

The following compounds of the formula I can be obtained analogously to examples 1 and 2 or as otherwise described hereinbefore. ($R_1$=H; $R_2$=$CH_3$).

| Cmpd. No. | $R_3$ | $R_4$ | $R_5$ | Position of $R_3$-bearing side chain | Configuration | Physical Data |
|---|---|---|---|---|---|---|
| 3 (a) | —C(CH$_3$)$_3$ | H | H | 3 | E | oil m.p.$^{(1)}$ = 160–165° |
| (b) | | | | | Z | oil |
| 4 (a) | C$_2$H$_5$<br>\|<br>—C(CH$_3$)$_2$ | H | H | 3 | E | oil |
| (b) | | | | | Z | oil |
| 5 (a) | " | H | H | 7 | E | oil m.p.$^{(1)}$ = 128–131° |
| (b) | | | | | Z | oil |
| 6 (a) | —C(CH$_3$)$_3$ | 3-Br | H | 7 | E | m.p. 51–57°:<br>m.p. $^{(1)}$ = 168–174° |
| (b) | | | | | Z | oil |
| 7 (a) | " | 4-Br | H | 7 | E | m.p. 55–58° |
| 8 (a) | " | 2-Cl | H | 7 | E | m.p. 67–70° |
| (b) | | | | | Z | oil |
| 9 (a) | " | H | H | 4 | E | oil m.p.$^{(1)}$ = 182–187° |
| (b) | | | | | Z | oil |
| 10 | " | 3-F | H | 7 | E | oil m.p.$^{(1)}$ = 150–170° |
| 11 (a) | " | 3-Cl | H | 4 | E | oil m.p.$^{(1)}$ = 181–183° |
| (b) | | | | | Z | oil |
| 12 (a) | " | 3-CF$_3$ | H | 7 | E | oil m.p.$^{(1)}$ = 175–188° |
| (b) | | | | | Z | oil |
| 13 | " | 2-F | H | 7 | E | oil m.p.$^{(1)}$ = 141–151° |
| 14 | " | 2-Cl | H | 4 | E | oil m.p.$^{(1)}$ = 195–206° |
| 15 (a) | " | 3-COCH$_3$ | H | 7 | E | m.p. 101–107° |
| (b) | | | | | Z | oil |
| 16 (a) | " | 3-CH$_3$ | H | 7 | E | oil m.p.$^{(1)}$ = 185–187° |
| (b) | | | | | Z | oil |
| 17 (a) | —C=CH$_2$<br>\|<br>CH$_3$ | H | H | 7 | Z | oil m.p.$^{(1)}$ = 134–143° |
| (b) | | | | | Z | oil |
| 18 | —C(CH$_3$)$_3$ | 3-CH$_2$OH | H | 7 | E | oil |
| 19 | " | 3-CHO | H | 7 | E | oil |
| 20 (a) | " | 2-Cl | 3-Cl | 7 | E | m.p. 82° |
| (b) | | | | | Z | oil |
| 21 (a) | " | 3-CN | H | 7 | E | oil m.p.$^{(1)}$ = 188–192° |
| (b) | | | | | Z | oil |
| 22 | " | 2-SCH$_3$ | 3-Br | 7 | E | m.p. 45–50° |
| 23 | " | 2-SCH$_3$ | H | 7 | E | oil |
| 24 | " | 3-CH=C(Br)$_2$ | H | 7 | E | oil m.p.$^{(1)}$ = 118–125° |

-continued

| Cmpd. No. | R₃ | R₄ | R₅ | Position of R₃-bearing side chain | Configuration | Physical Data |
|---|---|---|---|---|---|---|
| 25 | " | 3-C≡CH | H | 7 | E | oil |
| 26 | " | 3-COOCH₃ | H | 7 | E | oil |
| 27 | " | 3-CH=CH₂ | H | 7 | E | oil |
| 28 | " | 3-CH=CHCN | H | 7 | E | oil |
| 29 | " | 2-Br | 3-CN | 7 | E | oil |
| 30 | " | 3-CH₂CN | H | 7 | E | oil |
| 31 | " | 3-CH₂OCH₃ | H | 7 | E | oil |

[1] = melting point of hydrochloride

NMR-Spectra (δ,CDCl₃, TMS-Standard):

1 (a) E 7,7 (dd, J=7 u. 2Hz, 1H); 7,2–7,5 (m, 4H); 6,16 (dt, J=16 u. 2×6,5Hz, 1H); 5,66 (dt, J=16 u. 2×1Hz, 1H); 3,74 (s, 2H); 3,10 (dd, J=6,5 u. 1Hz, 2H); 2,2 (s, 3H); 1,22 (s, 9H).

(b) Z 7,7 (dd, J=7 u. 2Hz, 1H); 7,15–7,45 (m, 4H); 6,04 (dt, J=11 u. 2×7Hz, 1H); 5,6 (dt, J=11 u. 2×1Hz, 1H); 3,78 (s, 2H); 3,34 (dd, J=7 u. 1Hz, 2H); 2,24 (s, 3H); 1,24 (s, 9H).

2 (a) E 7,78 (dd, J=7 u. 2Hz, 1H); 7,25–7,5 (m, 3H); 6,16 (dt, J=16 u. 2×6Hz, 1H); 5,65 (dt, J=16 und 2×1Hz, 1H); 3,76 (s, 2H); 3,10 (dd, J=6 u. 1Hz, 2H); 2,20 (s, 3H); 1,22 (s, 9H).

(b) Z 7,78 (dd, J=7 u. 2Hz, 1H); 7,2–7,5 (m, 3H); 6,05 (dt, J=11 u. 2×6,5Hz, 1H); 5,63 (dt, J=11 u. 2×1Hz, 1H); 3,8 (s, 2H); 3,33 (dd, J=6,5 u. 1Hz, 1H); 2,24 (s, 3H); 1,24 (s, 9H).

3 (a) E 7,8–8,05 (m, 2H); 7,25–7,5 (m, 3H); 6,16 (dt, J=16 u. 2×6,5Hz, 1H); 5,66 (dt, J=16 u. 2×1Hz, 1H); 3,7 (s, 2H); 3,1 (dd, J=6,5 u. 1Hz, 2H); 2,24 (s, 3H); 1,24 (s, 9H).

(b) Z 7,8–8,0 (m, 2H); 7,2–7,5 (m, 3H); 6,0 (dt, J=11 u. 2×6,5Hz, 1H); 5,63 (dt, J=11 u. 2×1Hz, 2H); 3,72 (s, 2H); 3,3 (dd, J=6,5 u. 1Hz, 2H); 2,24 (s, 3H); 1,24 (s, 9H).

4 (a) E 7,8–8,1 (m, 2H); 7,25–7,5 (m, 3H); 6,18 (dt, J=16 u. 2×6,5Hz, 1H); 5,7 (dt, J=16 u. 1Hz, 1H); 3,72 (s, 2H); 3,12 (dd, J=6,5 u. 1Hz, 2H); 2,24 (s, 3H); 1,3–1,6 (psqu., 2H); 1,20 (s, 9H); 1,0 (s, 3H).

(b) Z 7,8–8,1 (m, 2H); 7,2–7,5 (m, 3H); 6,04 (dt, J=11 u. 2×7Hz, 1H); 5,67 (dt, J=11 u. 2×1Hz, 1H); 3,78 (s, 2H); 3,35 (dd, J=7 u. 1HZ, 2H); 2,3 (S, 3H); 1,3–1,6 (psqu., 2H); 1,22 (s, 9H); 1,02 (s, 3H).

5 (c) E 7,78 (dd, J=7 u. 2Hz, 1H); 7,25–7,5 (m, 4H); 6,20 (dt, J=16 u. 2×6,4Hz, 1H); 5,70 (dt, J=16 u. 2×1Hz, 1H); 3,77 (s, 2H); 3,12 (dd, J=6,4 u. 1Hz, 2H); 2,22 (s, 3H); 1,3–1,6 (m, 2H); 1,18 (s, 6H); 0,98 (ps.t, 3H).

(d) Z 7,88 (dd, J=6,5 u. 2,5Hz, 1H); 7,2–7,5 (m, 4H); 6,1 (dt, J=11 u. 2×7Hz, 1H); 5,65 (dt, J=11 u. 2×1Hz, 1H); 3,8 (s, 2H); 3,35 (dd, J=7 u. 1Hz, 1H); 2,26 (s, 3H); 1,3–1,7 (m, 2H); 1,2 (s, 6H); 1,0 (ps.t, 3H).

6 (a) E 7,77 (dd, J=7 u. 2Hz, 1H); 7,2–7,55 (m, 3H); 6,18 (dt, J=16 u. 2×6,5Hz, 1H); 5,66 (dt, J=16 u. 2×1Hz, 1H); 3,8 (s, 2H); 3,1 (dd, J=6,5 u. 1Hz, 2H); 2,22 (s, 3H); 1,24 (s, 9H).

(b) Z 7,88 (dd, J=7 u. 2Hz, 1H); 7,2–7,55 (m, 3H); 6,05 (dt, J=11 u. 2×6Hz, 1H); 5,64 (dt, J=11 u. 2×1Hz, 1H); 3,8 (s, 2H); 3,3 (dd, J=6 u. 1Hz, 2H); 2,24 (s, 3H); 1,24 (s, 9H).

7 (a) E 7,25–7,6 (m, 4H); 7,22 (dt, J=16 u. 2×7Hz, 1H); 6,70 (dt, J=16 u. 2×1Hz, 1H); 3,96 (s, 2H); 3,17 (dd, J=7 u. 1Hz, 1H); 2,25 (s, 3H); 1,24 (s, 9H).

8 (a) E 7,58 (dd, J=7 u. 2Hz, 1H); 7,1–7,4 (m, 3H); 6,20 (dt, J=16 u. 2×7Hz, 1H); 6,65 (dt, J=16 u. 1Hz, 1H); 3,68 (s, 2H); 3,08 (dd, J=7 u. 1Hz, 2H); 2,20 (s, 3H); 1,22 (s, 9H).

(b) Z 7,58 (dd, J=7 u. 2Hz, 1H); 7,1–7,4 (m, 3H); 6,08 (dt, J=11 u. 2×7Hz, 1H); 5,64 (dt, J=11 u. 2×1Hz, 1H); 3,72 (s, 2H); 3,34 (dd, J=7 u. 1Hz, 2H); 2,24 (s, 3H); 1,24 (s, 9H).

9 (a) E 7,5–7,85 (m, 2H); 7,2–7,45 (m, 3H); 6,12 (dt, J=16 u. 2×6,5Hz, 1H); 5,64 (dt, J=16 u. 2×1Hz, 1H); 3,76 (s, 2H); 3,10 (dd, J=6,5 u. 1Hz, 2H); 2,18 (s, 3H); 1,2 (s, 9H).

(b) Z 7,5–7,8 (m, 2H); 7,1–7,4 (m, 3H); 5,96 (dt, J=11 u. 2×6,5Hz, 1H); 5,6 (d, J=11Hz, 2H); 3,78 (s, 2H); 3,30

-continued

NMR-Spectra (δ,CDCl₃, TMS-Standard):

(d, J=6,5Hz, 2H); 2,20 (s, 3H); 1,24 (s, 9H).

10 (a) E 7.70 (dd, J=7.5 u. 2.0Hz, 1H); 7.38 (t, J=7.5Hz, 1H); 7.28 (dd, J=7.5 u. 2.0Hz, 1H); 6.84 (d, J=2.5Hz, 1H); 6.19 (dt, J=16 u. 2×6.5Hz, 1H); 5.68 (dt, J=16 u. 2×1.5Hz, 1H); 3.76 (s, 2H); 3.10 (dd, J=6.5 u. 1.5Hz, 2H); 2.21 (s, 3H); 1.22 (s, 9H).

11 (a) E 7.73 (dd, J=7.5 u. 2.0Hz, 1H); 7.42 (dd, J=7.5 u. 2.0Hz, 1H); 7.32 (t, J=7.5Hz, 1H); 7.31 (s, 1H); 6.12 (dt, J=16 u. 2×6.5Hz, 1H); 5.65 (dt, J=16 u. 2×1.5Hz, 1H); 4.15 (s, 2H); 3.16 (dd, J=6.5 u. 1.5Hz, 1H); 2.23 (s, 3H); 1.24 (s, 9H).

(b) Z 7.73 (dd, J=7.5 u. 2.0Hz, 1H); 7.42 (dd, J=7.5 u. 2.0Hz, 1H); 7.32 (t, J=7.5Hz, 1H); 7.32 (s, 1H); 6.0 (dt, J=11 u. 2×7Hz, 1H); 5.63 (dt, J=11 u. 2×1.2Hz, 1H); 4.19 (s, 2H); 3.42 (dd, J=6.5 u. 1.5Hz, 2H); 2.26 (s, 3H); 1.26 (s, 9H).

12 (a) E 7.90 (s, 1H); 7.86 (1H); 7.42 (t, J=7.5Hz, 1H); 7.25 (1H); 6.16 (dt, J=16 u. 2×6.5Hz, 1H); 5.65 (d, J=16 u. 2×1.5Hz, 1H); 3.78 (s, 2H); 3.10 (dd, J=6.5 u. 1.5Hz, 2H); 2.22 (s, 3H); 1.24 (s, 9H).

(b) Z 7.89 (s, 1H); 7.86 (1H); 7.42 (t, 2×7.5Hz, 1H); 7.30 (1H); 6.04 (dt, J=11 u. 2×7Hz, 1H); 5.64 (dt, J=11 u. 2×1.2Hz, 1H); 3.80 (s, 2H); 3.33 (dd, J=6.5 u. 1.5Hz, 2H); 2.24 (s, 3H); 1.24 (s, 9H).

13 E 7.52 (dd, J=7.5 u. 2.0Hz, 1H); 7.28 (t, J=7.5Hz, 1H); 7.12 (dd, J=7.5 u. 2.0Hz, 1H); 6.69 (d, J=3.0Hz, 1H); 6.18 (dt, J=16 u. 2×6.5Hz, 1H); 5.68 (dt, J=16 u. 1.5Hz, 1H); 3.68 (s, 2H); 3.10 (dd, J=6.5 u. 1.5Hz, 2H); 2.21 (s, 3H); 1.23 (s, 9H).

14 E 7.63 (m, 1H); 7.49 (d, J=1HZ, 1H); 7.25 (m, 2H); 6.14 (dt, J=16 u. 2×6.5Hz, 1H); 5.66 (dt, J=16 U. 2× 1.5Hz, 1H); 3.68 (s, 2H); 3.08 (dd, J=6.5 u. 1.5Hz, 2H); 2.20 (s, 3H); 1.24 (s, 9H).

15 (a) E 8.72 (dd, J=7.5 u. 2.0Hz, 1H); 8.30 (s, 1H); 7.45 (t, J=7.5Hz, 1H); 7.27 (m, 1H); 6.18 (dt, J=16 u. 2×6.5Hz, 1H); 5.68 (dt, J=16 u. 2×1.5Hz, 1H); 3.78 (s, 2H); 3.11 (dd, J=6.5 u. 1.5Hz, 2H); 2.64 (s, COCH₃); 2.21 (s, 3H); 1.24 (s, 9H).

(b) Z 8.72 (dd, J=7.5 u. 2.0Hz, 1H); 8.30 (s, 1H); 7.46 (t, J=7.5Hz, 1H); 7.30 (m, 1H); 6.06 (dt, J=11 u. 2×7Hz, 1H); 5.66 (dt, J=11 u. 1.2Hz, 1H); 3.82 (s, 2H); 3.35 (dd, J=6.5 u. 1.5Hz, 2H); 2.65 (s, COCH₃); 2.24 (s, 3H); 1.25 (s, 9H).

16 (a) E 7.68 (dd, J=7.5 u. 2.0Hz, 1H); 7.40 (t, J=7.5Hz, 1H); 7.30 (m, 1H); 7.10 (qua, J=1Hz, 1H); 6.20 (dt, J=16 u. 2×6.5Hz, 1H); 5.70 (dt, J=16 u. 2×1.5Hz, 1H); 3.78 (s, 2H); 3.12 (dd, J=6.5 u. 1.5Hz, 2H); 2.46 (d. J=1Hz, 3H); 2.24 (s, 3H); 1.25 (s, 9H).

(b) Z 7.68 (dd, J=7.5 u. 2.0Hz, 1H); 7.40 (t, J=7.5Hz, 1H); 7.30 (m, 1H); 7.10 (qua, J=1Hz, 1H); 6.09 (dt, J=11 u. 2×7Hz, 1H); 5.66 (dt, J=11 u. 2×1.2Hz, 1H); 3.81 (s, 2H); 3.36 (dd, J=6.5 u. 1.5Hz, 2H); 2.47 (d. J=1Hz, 3H); 2.28 (s, 3H); 1.27 (s, 9H).

17 (a) E 7.75 (dd, J=7.5 u. 2.0Hz, 1H); 7.2–7.5 (m, 4H); 6.30 (dt, J=16 u. 2×6.5Hz, 1H); 5.81 (dt, J=16 u. 2× 1.5Hz, 1H); 5.2–5.4 (m, 2H); 3.77 (s, 2H); 3.14 (dd, J=6.5 u. 1.5Hz, 2H); 2.23 (s, 3H); 1.90 (m, 3H).

(b) Z 7.75 (m, 1H); 7.2–7.5 (m, 4H); 6.19 (dt, J=11 u. 2×7Hz, 1H); 5.75 (dt, J=11 u. 2×1.5Hz, 1H); 5.2–5.4 (m, 2H); 3.81 (s, 2H); 3.37 (dd, J=6.5 u. 1.5Hz, 2H); 2.28 (s, 3H); 1.93 (m, 3H).

18 E 7.80 (dd, J=7.5 u. 2.0Hz, 1H); 7.38 (t, J=7.5Hz, 1H); 7.41 (s, 1H); 7.30 (m, 1H); 6.18 (dt, J=16 u. 2×6.5Hz, 1H); 5.68 (dt, J=16 u. 2×1.5Hz, 1H); 4.95 (d, J=1Hz, 1H); 3.77 (s, 2H); 3.10 (dd, J=6.5 u. 1.5Hz, 2H); 2.23

-continued

NMR-Spectra (δ,CDCl₃, TMS-Standard):

|    |     |   |   |
|----|-----|---|---|
|    |     |   | (s, 3H); 1.24 (s, 9H). |
| 19 | | E | 10.17 (s, 1H); 8.66 (dd, J=7.5 u. 2.0Hz, 1H); 8.35 (s, 1H); 7.47 (t, J=7.5Hz, 1H); 7.30 (m, 1H); 6.18 (dt, J=16 u. 2×6.5Hz, 1H); 5.70 (dt, J=16 u. 1.5Hz, 1H); 3.80 (s, 2H); 3.12 (dd. J=6.5 u. 1.5Hz, 2H); 2.23 (s, 3H); 1.25 (s, 9H). |
| 20 | (a) | E | 7.68 (dd, J=7.5 u. 2Hz, 1H); 7.4 (t, J=7.5Hz, 1H); 7.15-7.35 (m, 1H); 6.20 (dt, J=16 u. 2×6.5Hz, 1H); 5.65 (dt, J=16 u. 2×1.5Hz, 1H); 3.75 (s, 2H); 3.10 (dd, J=6.5 u. 1.5Hz, 2H); 2.20 (s, 3H); 1.22 (s, 9H). |
|    | (b) | Z | 7.68 (dd, J=7.5 u. 2Hz, 1H); 7.4 (t, J=7.5Hz, 1H); 7.15-7.3 (m, 1H); 6.08 (dt, J=11 u. 2×6.5Hz, 1H); 5.65 (dt, J=11 u. 2×1.5Hz, 1H); 3.78 (s, 2H); 3.34 (dd, J=6.5 u. 1.5Hz, 2H); 2.24 (s, 3H); 1.24 (s, 9H). |
| 21 | (a) | E | 8.18 (s, 1H); 7.95 (dd, J=7.5 u. 2Hz, 1H); 7.5 (t, J=7.5Hz, 1H); 7.25-7.4 (m, 1H); 6.2 (dt, J=16 u. 2×6.5Hz, 1H); 5.70 (dt, J=16 u. 2×1.5Hz, 1H); 3.82 (s, 2H); 3.14 (dd, J=6.5 u. 1.5Hz, 1H); 2.22 (s, 3H); 1.24 (s, 9H). |
|    | (b) | Z | 8.18 (s, 1H); 7.96 (dd, J=7.5 u. 1.5Hz, 2H); 7.52 (t, J=7.5Hz, 1H); 6.08 (dt, J=11 u. 2×6.5Hz, 1H); 5.68 (dt, J=11 u. 2×1.5Hz, 1H); 3.86 (s, 2H); 3.36 (dd, J=6.5 u. 1.5Hz, 2H); 2.26 (s, 3H); 1.26 (s, 9H). |
| 22 | | E | 7.62 (dd, J=7.5 u. 2Hz, 1H); 7.35 (t, J=7.5Hz, 1H); 7.18 (dd, J=7.5 u. 2Hz, 1H); 6.15 (dt, J=16 u. 2×6.5Hz, 1H); 5.67 (dt, J=16 u. 2×1.5Hz, 1H); 3.74 (s, 2H); 3.10 (dd, J=6.5 u. 1.5Hz, 2H); 2.64 (s, 3H); 2.22 (s, 3H); 1.24 (s, 9H). |
| 23 | | E | 7.55 (dd, J=7.5 u. 2Hz, 1H); 7.26 (t, J=7.5Hz, 1H); 7.19 (s, 1H); 7.13 (dd, J=7.5 u 2Hz, 1H); 6.16 (dt, J=16 u. 2×6.5Hz, 1H); 5.67 (dt, J=16 u. 2×1.5Hz, 1H); 3.69 (s, 2H); 3.10 (dd, J=6.5 u. 1.5Hz, 2H); 2.61 (s, 3H); 2.21 (s, 3H); 1.24 (s, 9H). |
| 24 | | E | 8.1 (d, J=1.5Hz, 1H); 7.7 (d, J=1.5Hz, 1H); 7.68 (dd, J=7.5 u. 2Hz, 1H); 7.4 (t, J=7.5Hz, 1H); 7.2-7.4 (m, 1H); 6.2 (dt, J=16 u. 2×6.5Hz, 1H); 5.58 (dt, J=16 u. 2×1.5Hz, 1H); 3.78 (s, 2H); 3.10 (dd, J=6.5 u. 1.5Hz, 2H); 2.2 (s, 3H); 1.22 (s, 9H). |
| 25 | | E | 7.9 (dd, J=7.5 u. 2Hz, 1H); 7.74 (s, 1H); 7.4 (d, J=7.5Hz, 1H); 7.3 (dd, J=7.5 u. 2Hz, 1H); 6.18 (dt, J=16 u. 2×6.5Hz, 1H); 5.68 (dt, J=16 u. 2×1.5Hz, 1H); 3.78 (s, 2H); 3.3 (s, 1H); 3.1 (dd, J=7.5 u. 1.5Hz, 2H); 2.22 (s, 3H); 1.24 (s, 9H); |
| 26 | | E | 8.55 (dd, J=7.5 u. 2Hz, 1H); 8.42 (s, 1H); 7.45 (t, J=7.5Hz, 1H); 7.3 (m, 1H); 6.18 (dt, J=16 u. 2×6.5Hz, 1H); 5.66 (dt, J=16 u. 2×1.5Hz, 1H); 3.95 (s, 3H); 3.78 (s, 2H); 3.1 (dd, J=6.5 u. 1.5Hz, 2H); 2.2 (s, 3H); 1.22 (s, 9H). |
| 27 | | E | 7.86 (dd, s=7.5 u. 2Hz, 1H); 7.2-7.7 (m, 3H); 7.02 (ddd, J=18,12 u. 1Hz, 1H); 6.2 (dt, J=16 u. 2×6.5Hz, 1H); 5.8 (dd, J=18 u. 1.5Hz, 1H); 5.65 (dt, J=16 u. 2×1.5Hz, 1H); 5.38 (dd, J=12 u. 1.5Hz, 1H); 3.78 (s, 2H); 3.1 (dd, J=6.5 u. 1.5Hz, 2H); 2.22 (s, 3H); 1.22 (s, 9H). |
| 28 | | E | 7.84 (dd, J=7.5 u. 2Hz, 1H); 7.80 (s, 1H); 7.7 (d, J=16Hz, 1H); 7.45 (t, J=7.5Hz, 1H); 7.34 (m, 1H); 6.18 (dt, J=16 u. 2×6.5Hz, 1H); 5.94 (d, J=16H); 5.68 (dt, J=16 u. 2×1.5Hz, 1H); 3.78 (s, 2H); 3.1 (dd, J=6.5 u. 1.5Hz, 2H); 2.2 (s, 3H); 1.22 (s, 9H). |
| 29 | | E | 7.76 (dd, J=7.5 u. 2Hz, 1H); 7.42 (t, J=7.5Hz, 1H); 7.24 (dd, J=7 u. 2Hz, 1H); 6.16 (dt, J=16 u. 2×6.5Hz, 1H); 5.64 (dt, J=16 u. 2×1.5Hz, 1H); 3.74 (s, 2H); 3.12 (dd, J=6.5 u. 1.5Hz, 2H); 2.2 (s, 3H); 1.22 (s, 9H). |
| 30 | | E | 7.64 (dd, J=7.5 u. 2Hz, 1H); 7.5 (s, 1H); 7.42 (t, J=7.5Hz, 1H); 7.32 (m, 1H); 6.2 (dt, J=16 u. 2×6.5Hz, 1H); 5.68 (dt, J=16 u. 2×1.5Hz, 1H); 3.9 (d, J=1Hz, 2H); 3.78 (s, 2H); 3.1 (dd, J=6.5Hz, 2H); 2.2 (s, 3H); 1.22 (s, 3H). |
| 31 | | E | 7.8 (dd, J=7.5 u. 2Hz, 1H); 7.7 (s, 1H); 7.4 (t, J=7.5Hz, 1H); 7.3 (m, 1H); 6.2 (dt, J=16 u. 2×6.5Hz, 1H); 5.7 (dt, J=16 u. 2×1.5Hz, 1H); 4.72 (d, J=1Hz, 2H); 3.78 (s, 2H); 3.42 (s, 3H); 3.1 (dd, J=6.5Hz, u. 1.5Hz, 2H); 2.22 (s, 3H); 1.25 (s, 9H). |

The required starting materials can be prepared for example as follows:

(A) 7-Bromomethylbenzo[b]thiophene 7 g of 7-methylbenzo[b]thiophene, 8,5 g of N-bromosuccinimide and a spatula tip of α,α'-azoisobutyronitrile are refluxed together for 6 hours in 50 ml of carbon tetrachloride. The resulting mixture is cooled, filtered and concentrated by evaporation. The resulting raw title compound can be directly employed in the next step. M.p. when isolated=57° (isopropanol)

The following compounds may be prepared analogously:

3-Bromo-7-bromomethylbenzo[b]thiophene
4-Bromo-7-bromomethylbenzo[b]thiophene
7-Bromomethyl-2-chlorobenzo[b]thiophene
7-Bromomethyl-3-chlorobenzo[b]thiophene, M.p.=75°-79° (ethanol)
7-Bromomethyl-3-fluorobenzo[b]thiophene, oil
4-Bromomethyl-3-chlorobenzo[b]thiophene
7-Bromomethyl-3-trifluoromethylbenzo[b]thiophene
7-Bromomethyl-2-fluorobenzo[b]thiophene
4-Bromomethyl-2-chlorobenzo[b]thiophene
3-Acetyl-7-bromomethyl[b]thiophene
7-Bromomethyl-3-cyanobenzo[b]thiophene
7-Bromomethyl-2,3-dichlorobenzo[b]thiophene
7-Bromomethyl-3-(2,2-dibromovinyl)benzo[b]thiophene
3-Ethynyl-7-bromomethylbenzo[b]thiophene
7-Bromomethyl-3-methoxycarbonyl-benzo[b]thiophene
7-Bromomethyl-3-(2-cyanovinyl)-benzo[b]thiophene
2-Bromo-7-bromomethyl-3-cyano-benzo[b]thiophene
7-Bromomethyl-3-cyanomethyl-benzo[b]thiophene
7-Bromomethyl-3-methoxymethyl-benzo[b]thiophene each of which may be employed directly in the next step.

(B) N-(7-Benzo[b]thienylmethyl)methanamine

7-Bromomethylbenzo[b]thiophene is dissolved in dichloromethane, added to 40 ml of a 33% solution of methylamine in ethanol and allowed to stand overnight. The resulting mixture is concentrated and the residue taken up in dichloromethane and extracted with 2N HCl. The aqueous phase is made strongly basic with NaOH and shaken with dichloromethane. The organic phase is dried with potassium carbonate, concentrated by evaporation and the residue vacuum distilled to produce the title product as an oil. B.p.=103°/1.3 mbar.

The following compounds may be prepared analogously:

N-(3-Chloro-7-benzo[b]thienylmethyl)methylamine: B.p.=130°-132°/1.3 Pascal, M.p. (hydrochloride)=250°-255°.
N-(3-Benzo[b]thienylmethyl)methylamine: B.p.=90°-94°/1.3 Pascal.
N-(3-Cyano-7-benzo[b]thienylmethyl)methylamine: M.p. (hydrochloride)=280°-285°.
N-(6,6-dimethyl-hept-2-en-4-ynyl)methylamine (Z,E-mixture): Following chromatography on silica gel (toluene/ethylacetate=4/1). NMR: 5.3-6.3 (m, 2H); [3.4 (d, J=6H)+3.16 (d, J=6 Hz), 2H]; 2,38 (s, 3H); 1.46 (s, 1H); 1.21 (s, 9H).
N-(3-Bromo-7-benzo[b]thienylmethyl)methylamine: M.p. (hydrochloride)=260°-262°.

(C) 3-Bromo-7-methylbenzo[b]thiophene 25 g of 7-methylbenzo[b]thiophene are dissolved in chloroform and 27 g of bromine added at room temperature with stirring. After one hour the mixture is poured onto water and the organic phase separated, washed, dried and concentrated under vacuum. The title compound (contaminated with ca. 10% of 4-bromo-7- methylbenzo[b]thiophene) is obtained as an oil following vacuum distillation at 92°–98°/2.6 mbar.

(D) 2-Chloro-7-methylbenzo[b]thiophene 2 g of 7-methylbenzo[b]thiophene are dissolved in abs. ether, 8.4 ml of an 1.6M solution of butyllithium in hexane added dropwise at −10° and the resulting mixture stirred for one hour at 0° to −5°. 1 g of gaseous chlorine is then added at −30° and, after removal of the cool bath, the mixture warmed to room temperature. After ca. one hour the mixture is repeatedly washed with water, dried and concentrated on a rotary evaporator.

The resulting title compound is reacted directly further. 2-Bromo-3-cyano-7-methyl-benzo[b]thiophene and 2-Chloro-4-methylbenzo[b]thiophene may be prepared analogously.

NMR: of the former 7.76 (dd, J=7.5 u. 2 Hz, 1H); 7.46 (t, J=7.5 Hz, 1H); 7.26 (dd, J=7.5 u. 2 Hz, 1H); 2.54 (s, 3H).

(E) 2,3-Dichloro-7-methylbenzo[b]thiophene 20 g of 7-methylbenzo[b]thiophene are dissolved in carbon tetrachloride and saturated with gaseous chlorine at room temperature. After 2 hours the excess chlorine is removed, the mixture concentrated on a rotary evaporator and the residue taken up in dichloromethane, washed with saturated aqueous NaHCO$_3$, dried and concentrated on a rotary evaporator. The title compound is obtained, following crystallisation from methanol, as colourless crystals. M.p.=48°–50°. 2,3-Dichloro-4-methylbenzo[b]thiophene may be prepared analogously.

(F) 3-Chloro-7-methylbenzo[b]thiophene 10 g of 2,3-Dichloro-7-methylbenzo[b]thiophene are dissolved in 200 ml ether and 28.8 ml of a 1.6M solution of butyllithium in hexane added dropwise at 0°. After one hour the mixture is poured into dilute aqueous HCl, the organic phase separated, washed, dried and concentrated on a rotary evaporator. The raw title product thus obtained is reacted directed further (B.p.=60°–62°/0.13 Pascal. 3-Chloro-4-methylbenzo[b]thiophene may be prepared analogously.

(G) 3-Fluoro-7-methylbenzo[b]thiophene 50 ml of a 1.6M solution of butyllithium in abs. ether are added dropwise at −78° to a solution of 18.1 g of 3-bromo-7-methylbenzo[b]thiophene in abs. ether. After 20 Minutes 9 g of perchlorylfluoride are introduced under inert gas and with stirring whereby the reaction temperature is maintained below −60°. The resulting mixture is stirred for 30 minutes at −78° and then slowly warmed to 0°, mixed with water and the organic phase separated, washed, dried and concentrated under vacuum. The residue is chromatographed over silica gel (eluant: hexane) to obtain the title compound as an oil.

(H) 7-Methyl-3-trifluoromethylbenzo[b]thiophene

A mixture of 2 g of 3-bromo-7-methylbenzo[b]thiophene, 4.8 g of CF$_3$COONa, 3 g CuI and 20 ml of 1-methylpyrrolidone are vigorously stirred and heated at 160°. After a short while evolution of gas commences. Stirring is continued for one hour at 160° and a further hour at 180°. After cooling the reaction mixture is poured into water, extracted with ether/hexane (1/1) and the organic phase washed, dried and concentrated under vacuum. The raw product is chromatographed over silica gel (eluant: n-hexane) and the title compound obtained as a colourless oil.

(I) 2-Fluoro-7-methylbenzo[b]thiophene

To a solution of 7 g of 7-methylbenzo[b]thiophene in abs. tetryhydrofuran are added dropwise at −78°, 30 ml of a 1.6M solution of n-butyllithium in hexane. After 20 minutes 5.5 g of perchloryl fluoride are introduced whereby the reaction temperature is maintained below −60°. After 30 minutes at −78° the temperature is slowly raised to 0°. The mixture is then mixed with water and the organic phase separated, washed, dried and concentrated under vacuum. The residue is chromatographed (eluant: n-hexane) to obtain the title compound as an oil.

(J) 3-Acetyl-7-methylbenzo[b]thiophene 420 mg of borontrifluoride-etherate are added to a mixture of 2 g of 7-methylbenzo[b]thiophene and 1.4 ml acetanhydride at 50° and the mixture warmed to 60° for 80 minutes. The resulting mixture is poured onto ice, extracted with ether and the organic phase washed, dried and concentrated on a rotary evaporator. The residue is chromatographed on silica gel (eluant: n-hexane) to obtain the title compound, contaminated with the 2-acetylisomer, as an oil for direct further reaction.

(K) N-(3-Methyl-7-benzo[b]thienylmethyl)methylamine (a) N-(t.-butoxycarbonyl)-N-(3-cyano-7-benzo[b]thienylmethyl)methylamine 3.6 g of N-(3-cyano-7-benzo[b]thienylmethyl)methylamine and 3.9 g of di-t.-butyldicarbonate are stirred in dichloromethane for one hour at room temperature. The solution is concentrated under vacuum and the resulting title compound directly further reacted. R$_f$=0.9 (in chloroform/ethanol=95/5).

NMR: 8.15 (s, 1H); 7.9 (d, 1H); 7.2–7.7 (m, 2H); 4.75 (s, 2H); 2.8 (s, 3H); 1.5 (s, 9H).

(b) N-(t.-butoxycarbonyl)-N-(3-formyl-7-benzo[b]thienylmethyl)methylamine 1.44 g of N-(t.-butoxycarbonyl)-N-(3-cyano-7-benzo[b]thienylmethyl)methylamine are taken up in abs. ether and 4 ml of a 1.2M solution of disobutylaluminium hydride in toluene added dropwise at 0°. Stirring is continued for one hour at room temperature and the mixture then poured into ice-cooled 2N acetic acid and extracted with ether and the organic phase washed neutral, dried and concentrated under vacuum. The oily title compound is directly further reacted.

NMR: 10.1 (s, 1H, CHO); 8.6 (dd, 1H); 8.35 (s, 1H); 7.2–7.7 (m, 2H); 4.8 (s, 2H); 2.8 (s, 3H); 1.55 (s, 9H); 3-Formyl-7-methylbenzo[b]thiophene: M.p.=55°–60° may be prepared analogously.

NMR: 10.0 (s, 1H); 8.4 (d, 1H); 8.2 (s, 1H); 7.1–7.7 (m, 2H); 2.55 (s, 3H).

(c) N-(t.-butoxycarbonyl)-N-(3-methyl-7-benzo[b]thienylmethyl)methylamine 5.1 g of N(t.-butoxycarbonyl)-N-(3-formyl-7-benzo[b]thienylmethyl)methylamine and 12 ml of hydrazinehydrate (85%) are warmed at 160° for 10 minutes in 40 ml of diethylglycol, cooled, 3.17 g of pulverized potassium hydroxide added and the mixture heated for one hour at 170°. Following cooling the reaction mixture is poured onto ice and extracted with ether and the organic phase washed, dried and concentrated under vacuum to give the title compound which is directly further reacted.

NMR: 7.2–7.8 (m, 4H); 4.7 (s, 2H); 2.8 (s, 3H); 2.4 (s, 3H); 1.5 (s, 9H).

(d) N-(3-methyl-7-benzo[b]thienylmethyl)methylamine 4 g of N-(t.-butoxycarbonyl)-N-(3-methyl-7-benzo[b]thienylmethyl)methylamine are stirred for half an hour at 0° in 15 ml of trifluoroacetic acid. The mixture is then poured onto ice, made alkaline with NaOH and extracted with ether and the organic phase washed, dried and concentrated under vacuum. The title substance is directly further reacted. $R_f=0.15$ (in chloroform/ethanol=95/5). N-(3-Vinyl-7-benzo[b]thienylmethyl)methylamine: oil; N-(3-hydroxymethyl-7-benzo[b]thienylmethyl)methylamine: oil; and N-(3-Formyl-7-benzo[b]thienylmethyl)methylamine: oil may be prepared analogously.

(L) 1-Bromo-6-methyl-2,6-heptadien-4-yne (a) 6-Methyl-1,6-heptadien-4-yn-3-ol 10 g Isopropenylacetylene are taken up in abs. tetrahydrofuran and under an inert gas 94.5 ml of 1.6M solution of n-butyllithium in hexane added dropwise at −20°. The mixture is then cooled to −78° and 8.5 g of acrolein added dropwise. The reaction mixture is warmed to room temperature, poured into saturated aqueous NH4Cl and repeatedly extracted with ether. The organic phase is washed, dried and concentrated in vacuum. An oil is obtained.

NMR: 6.02 (ddd, J=17, 10 u. 5.5 Hz, 1H); 5.0 (m, 1H); 5.2–5.55 (m, 2H); 1.9 (dd, J=1.4 u. 1 Hz, 3H).

(b) 1-Bromo-6-methyl-2,6-heptadien-4-yne

An alcoholic solution of 6-methyl-1,6-heptadien-4-yn-3-ol is added dropwise to 40 ml of fuming HBr and the mixture reacted for 1.5 hours at room temperature. The reaction mixture is poured onto ice and extracted with hexane. The organic phase is repeatedly washed with aqueous NaCl, dried and concentrated on a rotary evaporator. The oily reaction product consists (according to NMR) of a 3:1 mixture of (E)- and (Z)-1-bromo-6-methyl-2,6-heptadien-4-yne and is directly employed for further reaction.

NMR: (pure E-isomer): 6.28 (dt, J=15.5 u. 2×7 Hz, 1H); 5.85 (d, J=15.5 Hz, 1H); 4.0 (dd, J=7 u. 0.7 Hz, 2H); 5.2–5.4 (m, 2H); 1.90 (dd, J=1 u. 1.4 Hz, 1H).

(M) N-(t.-butoxycarbonyl)-N-(3-hydroxymethyl-7-benzo[b]thienylmethyl)methylamine 600 mg of N-(t.-butoxycarbonyl)-N-(3-formyl-7-benzo[b]thienylmethyl)methylamine are dissolved in ethanol, reacted with 100 mg NaBH4 and stirred for 2 hours at room temperature. The reaction mixture is concentrated, the residue partitioned between ether and water and the organic phase washed, dried and concentrated on a rotary evaporator. The oily title compound is directly further reacted. 3-Hydroxymethyl-7-methyl-benzo[b]thiophene may be prepared analogously.

(N) 3-Cyano-7-methylbenzo[b]thiophene 3 g of 3-bromo-7-methylbenzo[b]thiophene and 1.1 g CuCN are dissolved in dry pyridine and heated at 220° in an autoclave for 12 hours. The mixture is cooled, concentrated, the residue partitioned between dichloromethane and dilute HCl and the organic phase washed, dried and concentrated. Chromatography of the residue over silica gel (toluene) yields the title compound as pale-yellow crystals. M.p.=82°–84°.

(O) N-(2-methylthio-3-bromo-7-benzo[b]thienylmethyl)methylamine

To a solution of 2.55 g of N-(3-bromo-7-benzo[b]thienylmethyl)methylamine in abs. ether are added dropwise under inert gas at −70° 13.8 ml (2 equivalents) of a 15% solution of n-butyllithium in n-hexane. 1.9 ml of dimethyldisulfide are then added slowly at −70° and the reaction mixture gradually warmed to room temperature. It is then poured into ice-cooled 2N HCl, shaken and the acid phase separated, made alkaline with NaOH and extracted with ether. The ether phase is dried, concentrated under vacuum and the oil thus obtained directly further reacted.

NMR: 7.2–7.7 (m, 3H); 4.0 (s, 2H); 2.6 (s, 3H); 2.45 (s, 3H); 1.5 (br, N-H).

(P) N-(2-methylthio-7-benzo[b]thienylmethyl)methylamine

To a solution of 0.3 g of N-(2-methylthio-3-bromo-7-benzo[b]thienylmethyl)methylamine in abs. ether are added dropwise under inert gas at −70°, 1.4 ml of a 15% solution of n-butyllithium in n-hexane and stirring continued at −70° for half an hour. The mixture is then poured into ice-cooled 2N HCl, shaken and the acidic phase separated, made alkaline with NaOH and extracted with ether. The ether phase is dried, concentrated in vacuum and the resulting oil directly further reacted.

(Q) 3-(2,2-Dibromovinyl)-7-methylbenzo[b]thiophene 1.04 g of Zn dust and 4.17 g of triphenylphosphine are taken up in dichloromethane and 5.27 of tetrabromomethane dissolved in dichloromethane added dropwise under inert gas and with cooling. Following stirring for 24 hours at room temperature 1.4 g of 3-formyl-7-methylbenzo[b]thiophene dissolved in dichloromethane are added dropwise with ice-cooling and stirring continued overnight at room temperature. Pentane is added and the precipitated Ph3PO filtered off. Evaporation of the filtrate under vacuum yields a residue which is chromatographed over silica gel to yield the title compound, M.p.=75°–78°.

(R) 3-Ethynyl-7-methylbenzo[b]thiophene 0.6 g of 3-(dibromovinyl)-7-methylbenzo[b]thiophene are dissolved in abs. tetrahydrofuran and 3.38 ml of a 15% solution of n-butyllithium in n-hexane are added dropwise under inert gas and at −78°. Stirring is continued for one hour at −78° and the mixture subsequently warmed to room temperature, poured into saturated aq. NaHCO3 and extracted with ether. The organic phase is washed, dried, concentrated and directly further reacted.

NMR: 7.85 (dd, J=7 u. 2 Hz, 1H); 7.70 (s, 1H); 7.40 (t, J=7 Hz, 1H); 7.20 (dd, J=7 and 2 Hz, 1H); 3.28 (s, 1H); 2.58 (s, 3H).

(S) N-(t.-Butoxycarbonyl)-N-(3-vinyl-7-benzo[b]thienylmethyl)methylamine 0.7 ml of a 15% solution of n-butyllithium in hexane are added dropwise under inert gas to a suspension of 0.43 g of methyltriphenylphosphonium bromide in abs. tetrahydrofuran and the mixture stirred for 1 hour at room temperature. A solution of 0.37 g N-(t.-butoxycarbonyl)-N-(3-formyl-7-benzo[b]thienylmethyl)methylamine in tetrahydrofuran is then added dropwise and the resulting mixture refluxed for 20 hours. The reaction mixture is poured onto ice, repeatedly extracted with ether and the organic phase washed, dried, concentrated and chromatographed over silica-gel (eluant: toluene/glacial acetic acid=9:1) to give the title compound as an oil.

NMR: 7.88 (dd, J=7.5 u. 2 Hz, 1H); 7.5 (s, 1H); 7.44 (t, J=7.5 Hz, 1H); 7.25 (dd, J=7.5 u.~1 Hz, 1H); 7.02 (ddd, J=18, 12 u.~1 Hz, 1H); 5.82 (dd, J=18 u.~1.5 Hz, 1H); 5.4 (dd, J=12 u. 1.5 Hz, 1H); 4.72 (s, 2H); 2.8 (s, 3H); 1.5 (s, 9H). 3-(2-Cyanovinyl)-7-methyl-benzo[b]thiophene may be prepared analogously.

NMR: 7.80 (s, 1H); 7.76 (dd, J=7.5 u. 2 Hz, 1H); 7.68 (d, J=16 Hz, 1H); 7.46 (t, J=7.5 Hz, 1H); 7.26 (m, 1H); 5.96 (d, J=16 Hz, 1H); 2.6 (s, 3H).

(T) 3-Cyanomethyl-7-methyl-benzo[b]thiophene 290 mg of 3-hydroxymethyl-7-methyl-benzo[b]thiophene are dissolved in ether, 0.6 ml SOCl$_2$ added and the mixture stirred for 2 hours at room temperature. The reaction mixture is poured onto ice and the organic phase washed neutral, dried and concentrated under vacuum. The crude 3-chloromethyl-7-methyl-benzothiophene thus obtained is dissolved in acetone, mixed with an aqueous solution of 170 mg of KCN and refluxed for 18 hours. The reaction mixture is concentrated, the residue partitioned between water and ether and the organic phase washed, dried, concentrated and chromatographed over silica-gel (eluant: toluene) to yield the title product is an oil.

NMR: 6.7–7.6 (m, 4H); 3.6 (br, 2H); 2.5 (s, 3H).

(U) 3-Methoxymethyl-7-methyl-benzo[b]thiophene 400 mg of 3-hydroxymethyl-7-methyl-benzo[b]thiophene are dissolved in tetrahydrofuran, mixed with 82 mg of NaH (80%) and after addition of 48 mg of methyl iodide heated for half an hour at 50° C. The reaction mixture is mixed with water, repeatedly extracted and the organic phase washed, dried and concentrated on a rotary evaporator. The residue is chromatographed over silica-gel (eluant: toluene/glacial acetic acid=95:5) to yield the title compound as an oil.

NMR: 7.2–7.9 (m, 4H); 4.75 (s, 2H); 3.5 (s, 3H); 2.66 (s, 3H).

I claim:

1. A compound of the formula

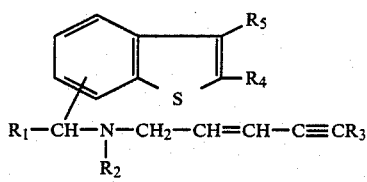

where
R$_1$ is hydrogen and R$_2$ is methyl,
R$_3$ is tertiary alkyl or alkenyl and
R$_4$ and R$_5$ are independently hydrogen, fluro, chloro, bromo, alkyl or trifluoromethyl
with the proviso that at least one of R$_4$ and R$_5$ is hydrogen, and the allylamine group

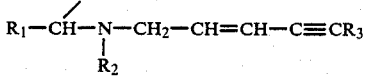

is in the 4-, 5-, 6-, or 7-position, in free base form or acid addition salt form.

2. A compound as claimed in claim 1, wherein the allylamine side 20 chain is in the 4- or 7-position.

3. A compound of the formula

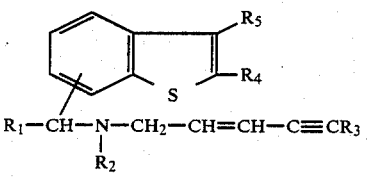

where
R$_1$ is hydrogen and R$_2$ is methyl,
R$_3$ is tertiary alkyl or alkenyl and
R$_4$ and R$_5$ are independently hydrogen, fluro, chloro, bromo, alkyl or trifluoromethyl
with the proviso that at least one of R$_4$ and R$_5$ is hydrogen, and the allylamine group

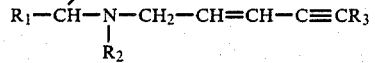

is in the 4-, or 7-position and the double bond proximal to the nitrogen has the trans(E) configuration, in free base form or acid addition salt form.

4. A compound according to claim 3 in which the allylamine group is in the 7-position,
R$_3$ is tertiary alkyl of 4 to 6 carbon atoms or alkenyl of 3 to 4 carbon atoms;
R$_4$ is hydrogen, fluoro or chloro and
R$_5$ is hydrogen, fluoro, chloro, bromo, methyl or trifluoromethyl,
in free base form or acid addition salt form.

5. A compound according to claim 3 in which the allylamine group is in the 4-position and
R$_3$ is tertiary alkyl of 4 to 6 carbon atoms;
R$_4$ is hydrogen or chloro and
R$_5$ is hydrogen,
in free base form or acid addition salt form 6. The compound according to claim 3, which is N-(7-benzo[b]thienylmethyl)-N-methyl-6,6-dimethyl-hept-2-en-4-ynamine, in free base form or in the form of an acid addition salt.

7. The compound according to claim 3 in which R$_3$, R$_4$, and R$_5$ are —C(CH$_3$)$_2$ C$_2$H$_5$, H and H respectively and the allylamine group is in the 7-position, in free base form or in acid addition salt form.

8. The compound according to claim 3 in which R$_3$, R$_4$, and R$_5$ are t-C$_4$H$_9$, H, and Br respectively and the allylamine group is in the 7-position, in free base form or in acid addition salt form.

9. The compound according to claim 3 in which R$_3$, R$_4$ and R$_5$ are -t-C$_4$H$_9$, Cl, and H respectively and the allylamine group is in the 7-position, in free base form or in acid addition salt form.

10. The compound according to claim 3 in which R$_3$, R$_4$, and R$_5$ are t-C$_4$H$_9$, H, and H respectively and the allylamine group is in the 4-position, in free base form or in acid addition salt form.

11. The compound according to claim 3 in which R$_3$, R$_4$, and R$_5$ are t-C$_4$H$_9$, H, and F respectively and the allylamine group is in the 7-position, in free base form or in the acid addition salt form.

12. The compound according to claim 3 in which R$_3$, R$_4$, and R$_5$ are t-C$_4$H$_9$, H, and Cl respectively and the allylamine group is in the 4-position, in free base form or in acid addition salt form.

13. The compound according to claim 3 in which R$_3$, R$_4$, and R$_5$ are t-C$_4$H$_9$, H, and CF$_3$ respectively and the allylamine group is in the 7-position, in free base form or in acid addition salt form.

14. The compound according to claim 3 in which R$_3$, R$_4$, and R$_5$ are t-C$_4$H$_9$, F, and H respectively and the allylamine group is in the 7-position, in free base form or in acid addition salt form.

15. The compound according to claim 3 in which R$_3$, R$_4$, and R$_5$ are t-C$_4$H$_9$, Cl, and H respectively and the allylamine group is in the 4-position, in free base form or in acid addition salt form.

16. The compound according to claim 3 in which $R_3$, $R_4$, and $R_5$ are t-$C_4H_9$, H, and $CH_3$ respectively and the allylamine group is in the 7-position, in free base form or in acid addition salt form.

17. The compound according to claim 3 in which $R_3$, $R_4$, and $R_5$ are

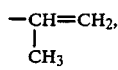

H, and H respectively and the allylamine group is in the 7-position, in free base form or in acid addition salt form.

18. (E)-N-(3-chloro-7-benzo[b]thienylmethyl)-N-methyl-6,6-dimethyl-hept-2-en-4-ynamine in free base form or in the form of an acid addition salt.

19. A chemotherapeutical composition comprising a compound as claimed in claim 1 in free base form or in the form of a chemotherapeutically acceptable acid addition salt together with a chemotherapeutically acceptable diluent or carrier.

20. A method of treating diseases or infections caused by mycetes which comprises administering to a subject in need of such treatment an effective amount of a compound of formula I as claimed in claim 1 in free base form or in the form of a chemotherapeutically acceptable acid addition salt.

21. A chemotherapeutical composition comprising a compound as claimed in claim 3 in free base form or in the form of a chemotherapeutically acceptable acid addition salt together with a chemotherapeutically acceptable diluent or carrier.

22. A method of treating diseases or infections caused by mycetes which comprises administering to a subject in need of such treatment an effective amount of a compound of formula I as claimed in claim 3 in free base form or in the form of a chemotherapeutically acceptable acid addition salt.

* * * * *